United States Patent [19]

Chow et al.

[11] Patent Number: 4,508,661

[45] Date of Patent: Apr. 2, 1985

[54] METHOD FOR THE DECOLORIZATION OF AROYL CHLORIDE COMPOSITIONS

[75] Inventors: Richard H. Chow, Williamsville; Emil J. Geering, Grand Island, both of N.Y.

[73] Assignee: Occidental Chemical Corporation, Niagara Falls, N.Y.

[21] Appl. No.: 523,237

[22] Filed: Aug. 15, 1983

[51] Int. Cl.$^3$ ............................................. C07C 51/64
[52] U.S. Cl. ................................................. 260/544 D
[58] Field of Search ................................... 260/544 D

[56] References Cited

U.S. PATENT DOCUMENTS

| 2,845,429 | 7/1958 | Carpino | 260/544 D |
| 4,069,191 | 1/1978 | Post | 523/461 |
| 4,104,300 | 8/1978 | Zoche et al. | 260/544 D |
| 4,294,777 | 10/1981 | Bockmann et al. | 260/544 D |

Primary Examiner—Natalie Trousof
Assistant Examiner—Bruce D. Gray
Attorney, Agent, or Firm—James F. Tao; Arthur S. Cookfair

[57] ABSTRACT

Aroyl chloride compositions are decolorized by contact with a solid, substantially insoluble, polyamide.

13 Claims, No Drawings

METHOD FOR THE DECOLORIZATION OF AROYL CHLORIDE COMPOSITIONS

BACKGROUND OF THE INVENTION

1. Field Of The Invention

This invention relates to a method for improving the color of aroyl chloride compositions.

Aroyl chlorides, such as benzoyl chloride, are used commercially in the manufacture of dye intermediates and of peroxides, such as benzoyl peroxide.

Aroyl chlorides are known to exhibit an undesireable tendency to become discolored during storage. Benzoyl chloride, for example, is a colorless liquid, and in commercial form is typically characterized by a color specification of less than 25 APHA. (APHA denotes a color unit system based on a visual comparison of a sample with standardized aqueous solution of potassium chloroplatinate and cobaltous chloride. The system is described in detail in Standard Methods for the Examination of Water and Wastewater, 15th ed., American Public Health Association, New York, 1981, p. 60–63). Frequently, while in storage or shipment in drums, trailers, tank cars and the like, benzoyl chloride will develop an undesireable color. Although the specific cause of discoloration is uncertain, it is considered that it may be related to the presence of iron or other metal contaminents in the aroyl chloride. Since the off-color material is generally unacceptable, it is often necessary to return and re-distill such material. The additional transportation, handling, and re-distillation may add substantially to the overall cost of the acid chloride. It will be apparent that a need exists for a simple inexpensive method to treat off-color material on-site, and thus eliminate the transportation and other costs associated with return and re-distillation.

MATERIAL INFORMATION DISCLOSURE STATEMENT

U.S. Pat. No. 4,294,777 discloses the stabilization of aromatic carboxylic acid chlorides against discoloration by addition thereto of a color stabilizer. The various color stabilizers disclosed include, for example, acetone, methyl ethyl ketone, diethyl ketone, benzaldehyde, acetophenone, ethyl acetoacetate, acrylic acid ethyl ester, methacrylic acid methyl ester, crotonic acid, vinyl acetate, maleic acid, maleic acid diethyl ester, fumaric acid diethyl ester, dicyclopentadiene, e-caprolactam, styrene, methyl vinyl ketone, acrolein, cyclohexene, ally chloride, cinnamic acid, allyl alcohol, acetaldehyde, methyl phosphite, triphenylphosphine, phosphorus trichloride, arsenic trichloride, methacrylic acid amide and cyclohexanone and others.

U.S. Pat. No. 4,104,300 discloses the removal of molybdenum catalyst residues from carboxylic acid chlorides by treatment with a complexing agent, prior to distillation. A wide variety of complexing agents are disclosed, including, for example, benzamide and e-caprolactam.

SUMMARY OF THE INVENTION

It has now been found that liquid aroyl chloride compositions may be decolorized by contact with a polyamide. The polyamide may be employed in various forms that provide a polyamide surface for contact with the liquid aroyl chloride composition. Thus, for example, the polyamide may be in particulate form, as a packed column through which the aroyl chloride composition is passed. Alternatively, the polyamide particles may be added to a container of the aroyl chloride and allowed to remain in continuous contact therewith. In other embodiments the aroyl chloride composition may be stored in nylon containers or nylon-lined containers or may be processed through nylon tubing or the like.

The polyamides suitable for use in the process of this invention include those polymers commonly known by the generic term, nylon, characterized by the presence of recurring amide groups as an integral part of the polymer chain. Included are the various nylon homopolymers, copolymers, and the like as well as blends thereof. Typical of the nylon compositions are polycaprolactam (nylon 6); the polyamides derived by condensation of dicarboxylic acid with a diamine, such as polyhexamethylene adipamide (nylon 66), polyhexamethylene sebacamide (nylon 610), and polyhexamethylene dodecanediamide (nylon 612), as well as copolymers and blends and the like such as nylon 66/6; nylon 66/610; nylon 66/612; nylon 66/610/6; nylon 66/612/6 and the like.

Aroyl chlorides that may be treated in accordance with the process of this invention are of the formula

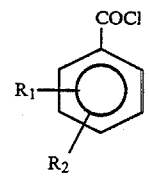

wherein $R_1$ and $R_2$ are independently selected from the group consisting of hydrogen, halogen, alkyl and alkoxy.

Suitable halogen substituents include fluorine, chlorine and bromine and most preferably chlorine.

Suitable alkyl and alkoxy groups include those having up to 10 carbon atoms and most preferably up to 4 carbon atoms, for example alkyl radicals such as methyl, ethyl, n-propyl, iso-propyl, n-butyl, iso-butyl, tert-butyl, n-pentyl, iso-pentyl, 2-methylpentyl, 3-methylpentyl, n-hexyl, n-heptyl, n-octyl, iso-octyl, n-nonyl, n-decyl and cyclohexyl, preferably methyl, ethyl, n-propyl, iso-propyl, n-butyl, iso-butyl and tert-butyl; and alkoxy radicals such as methoxy, ethoxy, propoxy, butoxy, pentyloxy and hexyloxy, preferably methoxy and ethoxy.

Aroyl chloride which may be color-stabilized in accordance with this invention, include for example, benzoyl chloride, o-toluic acid chloride, p-toluic acid chloride, 1-chlorobenzoyl chloride, 3-chlorobenzoyl chloride, 4-chloroebenzoyl chloride, 2,4-dichlorobenzoyl chloride, and anisic acid chloride.

DETAILED DESCRIPTION OF THE INVENTION

In a preferred embodiment, the process of this invention comprises passing a liquid aroyl chloride composition through a bed, such as a packed column of nylon particles.

The capacity of nylon particles to decolorize an aroyl chloride composition will depend on the surface area of nylon particles, the contact time, and the initial color of the aroyl chloride composition. Thus, for example, longer contact times will result in a greater decolorizing effect. The greater the surface area of the nylon particles, the greater the decolorizing effect and/or the lower the contact time required for the same degree of decolorization. Thus, for example, one kg of Nylon 612 particles having an average B.E.T. surface area of 0.09 m²/g has the capacity to reduce about 700 kg of 100 APHA color benzoyl chloride to 20 APHA color, whereas one kg of Nylon 612 particles having an average B.E.T. surface area of 0.05 m²/g can only decolorize about 160 kg of 100 APHA color benzoyl chloride to 20 APHA color.

The following specific examples are provided to further illustrate this invention and the manner in which it may be carried out. It will be understood, however, that the specific details given in the examples have been chosen for purpose of illustration and are not to be construed as a limitation on the invention. In the examples, unless otherwise indicated, all parts and percentages are by weight and all temperatures are in degrees Celsius.

EXAMPLES 1–5

To a 100 g sample of off-color benzoyl chloride was added 1 g of nylon 6 cylindrical pellets (approximately 0.25 cm diameter and 0.25 cm length). The mixture was shaken for about six hours, after which the nylon particles were separated. The color of the benzoyl chloride was determined spectrophotometrically before and after the treatment. The procedure was repeated, substituting pellets of various other nylon compositions, with the results shown in the table below.

| Sample No. | Nylon Type | Benzoyl Chloride Color (APHA) Initial | Final |
|---|---|---|---|
| 1 | Nylon 6 | 1407 | 40 |
| 2 | Nylon 66 | 1407 | 61 |
| 3 | Nylon 612 | 1407 | 17 |
| 4 | Nylon 11 | 1407 | 17 |
| 5 | Nylon 12 | 1407 | 18 |

EXAMPLE 6

A glass column approximately 2.5 cm diameter and 35 cm long was packed with approximately 50 g of 2 mm diameter nylon 612 particles. The nylon bed was approximately 30 cm long and had a 100 ml void volume. Glass wool was placed at each end to keep the nylon packing in place. A sample of off-color benzoyl chloride was analyzed by spectrophotometric methods and found to have a color of 1400 APHA. A one liter sample of the benzoyl chloride was treated by passing through the nylon bed at a flow rate of 10 ml/minute. Analysis of the treated benzoyl chloride indicated a color of 23 APHA. A second pass through the column at 10 ml/minute further reduced the color from 23 APHA to 17 APHA.

EXAMPLE 7

A sample of benzoyl chloride having color of greater than 90 APHA was treated by passing through a bed of nylon 612 particles in the manner described in Example 6. After the first pass through the nylon bed at 10 ml/minute, the color of the treated benzoyl chloride was found to be 20 APHA. A second pass at the same flow rate, reduced the color of the benoyl chloride product to 15 APHA.

EXAMPLE 8

Following the general procedure of Example 6 and 7 a quantity of off-color benzoyl chloride (315 APHA) was passed through a column of Nylon 612 particles at a flow rate of 12 ml/minute. The process was continued for about 5 hours with the results shown in the table below. At that time a rise in the APHA color of the product was observed, incicating depletion of the decolorizing capacity of the nylon particles.

| Time (Hours) | Product Color (APHA) | Total Volume Treated (Liters) |
|---|---|---|
| 1 | 15 | 0.72 |
| 2 | 15 | 1.44 |
| 3 | 15 | 2.16 |
| 4 | 15 | 2.88 |
| 4.5 | 15 | 3.24 |
| 5 | 18 | 3.60 |
| 5.2 | 40 | 3.75 |

What is claimed is:

1. A method for decolorizing an aroyl chloride of the formula

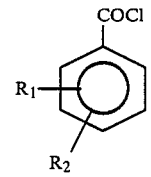

wherein $R_1$ and $R_2$ are independently selected from the group consisting of hydrogen, halogen, alkyl, and alkoxy, which comprises contacting the aroyl chloride with a polyamide.

2. A method according to claim 1 wherein the polyamide is a nylon.

3. A method according to claim 1 wherein the aroyl chloride is benzoyl chloride.

4. A method according to claim 3 wherein the polyamide is a nylon.

5. A method according to claim 4 wherein the nylon is in particulate form.

6. A method according to claim 4 wherein the nylon is selected from the group consisting of Nylon 6, Nylon 66, Nylon 612, Nylon 11, and Nylon 12.

7. A method according to claim 6 wherein the nylon in Nylon 6.

8. A method according to claim 6 wherein the nylon is Nylon 66.

9. A method according to claim 6 wherein the nylon is Nylon 612.

10. A method according to claim 6 wherein the nylon is Nylon 11.

11. A method according to claim 6 wherein the nylon is Nylon 12.

12. A method according to claim 6 wherein the nylon is in particulate form.

13. A method according to claim 12 which comprises passing benzoyl chloride through a packed column of nylon particles.

* * * * *